United States Patent
Schleipen et al.

(10) Patent No.: US 10,330,598 B2
(45) Date of Patent: Jun. 25, 2019

(54) BIOSENSOR COMPRISING WAVEGUIDE

(71) Applicant: KONINKLIJKE PHILIPS N.V., Eindhoven (NL)

(72) Inventors: Johannes Joseph Hubertina Barbara Schleipen, Endhoven (NL); Reinhold Wimberger-Friedl, Veldhoven (NL); Pieter Jan Van Der Zaag, Waalre (NL); Hendrik Paul Urbach, Prinsenbeek (NL); Mitradeep Sarkar, Orsay (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 15/100,346

(22) PCT Filed: Nov. 25, 2014

(86) PCT No.: PCT/EP2014/075444
§ 371 (c)(1),
(2) Date: May 31, 2016

(87) PCT Pub. No.: WO2015/082247
PCT Pub. Date: Jun. 11, 2015

(65) Prior Publication Data
US 2016/0299077 A1 Oct. 13, 2016

(30) Foreign Application Priority Data
Dec. 3, 2013 (EP) .................................. 13195407

(51) Int. Cl.
*G01N 21/64* (2006.01)
*G01N 21/77* (2006.01)
*C12Q 1/6869* (2018.01)

(52) U.S. Cl.
CPC ......... *G01N 21/648* (2013.01); *C12Q 1/6869* (2013.01); *G01N 21/6452* (2013.01);
(Continued)

(58) Field of Classification Search
CPC ............. G01N 21/648; G01N 21/6452; G01N 21/7743; C12Q 1/6869
(Continued)

(56) References Cited

U.S. PATENT DOCUMENTS

| | | | |
|---|---|---|---|
| 6,707,561 B1 | 3/2004 | Budach | |
| 8,868,156 B1 * | 10/2014 | Koops | G01J 3/02 |
| | | | 600/407 |

(Continued)

FOREIGN PATENT DOCUMENTS

| | | |
|---|---|---|
| WO | WO2006135782 A2 | 12/2006 |
| WO | WO2009001245 A1 | 12/2008 |
| WO | WO2012129068 A1 | 9/2012 |

OTHER PUBLICATIONS

Chien et al., "Coupled Waveguide-Surface Plasmon Resonance Biosensor with Subwavelength Grating", BiOsensOrs and Bi0electrOnics, Elsevier BV, NL, vol. 22, No. 11, Mar. 30, 2007, pp. 2737-2742, XP022006482.

(Continued)

*Primary Examiner* — Jill A Warden
*Assistant Examiner* — Jacqueline Brazin
(74) *Attorney, Agent, or Firm* — Larry Liberchuk

(57) ABSTRACT

The invention relates to an optical device (110) and a corresponding detection apparatus (100) that may for example be used for monitoring the replication of nucleotide sequences at a surface. In a preferred embodiment, the optical device (110) comprises a waveguide substrate (130) with a wiregrid (140) on a bottom surface (132), wherein apertures (141) of the wiregrid are in at least one direction
(Continued)

(x) smaller than a characteristic wavelength (λ) of input light (IL). Moreover, a diffractive structure (120) is disposed on the opposite surface (131) of the substrate (130) for coupling input light (IL) into the substrate (130) such that constructive interference occurs at the apertures (141). Thus evanescent waves can be generated with high efficiency in these apertures, allowing for example for a surface-specific excitation of fluorescence (FL) that can be sensed by a detector (160).

10 Claims, 5 Drawing Sheets

(52) U.S. Cl.
CPC . *G01N 21/7743* (2013.01); *G01N 2021/7773* (2013.01); *G01N 2021/7786* (2013.01); *G01N 2201/068* (2013.01); *G01N 2201/06113* (2013.01); *G01N 2201/08* (2013.01)

(58) Field of Classification Search
USPC ...................................... 422/82.11
See application file for complete search history.

(56) References Cited

U.S. PATENT DOCUMENTS

| | | |
|---|---|---|
| 2007/0014017 A1 | 1/2007 | Thome-Forster |
| 2010/0065726 A1* | 3/2010 | Zhong ................. G01N 21/648 250/227.24 |
| 2010/0096562 A1 | 4/2010 | Klunder |
| 2011/0195516 A1* | 8/2011 | Kahya .................... B82Y 15/00 436/172 |
| 2011/0210094 A1* | 9/2011 | Gray ................. G01N 21/6428 216/12 |

OTHER PUBLICATIONS

Thayil A et al., "Two-Photon Fluorescence Spectroscopy by Resonant Single and Double Grating Waveguide Structures", Lasers and Electr0-0ptics, 2005. (CLE0). C0nference 0n Baltim0re, MD, USA, Piscataway, NJ, USA,IEEE, vol. 1, May 22, 2005, pp. 752-754, XP010876707.

Lundquist et al., "Parallel Confocal Detection of Single Molecules in Real Time", Optics Leters, vol. 33, No. 9, May 1, 2008, pp. 1026-1028.

Eid, J. et al., "Real-Time DNA Sequencing from Single Polymerase Molecules ", Science, vol. 323, Jan. 2, 2009, pp. 133-138.

* cited by examiner

BIOSENSOR COMPRISING WAVEGUIDE

FIELD OF THE INVENTION

The invention relates to an optical device, a detector apparatus, and a method using a waveguide that may particularly be used in biosensing applications such as sequencing of nucleic acids.

BACKGROUND OF THE INVENTION

US 2010/096562 A1 discloses a medium having at least one planar structure with a plurality of apertures on one side. The apertures are in one direction smaller than a diffraction limit of the medium. Sample medium adjacent to the planar structure can be illuminated by evanescent waves through the apertures.

WO 2009/001245 A1 discloses a sensor comprising: (i) a substrate in which an excitation radiation having a predetermined wavelength may propagate; (ii) a wiregrid at a first side of said substrate, having at least one aperture or slit arranged for being filled with a medium which comprises at least one particle to be detected, the latter being to be excited via said excitation radiation; and (iii) at least on reflective means, arranged at a second side of said substrate which is opposite to the first side, to reflect towards the wiregrid at least a part of excitation radiation that propagate into the substrate and that has been reflected at least once by the wiregrid.

US 2010/0065726 A1 discloses substrates, methods and devices for use in various applications, including single-molecule analytical reactions. WO 2006/135782 A2 discloses a system for detecting separately and substantially simultaneously light emissions from a plurality of localized light-emitting analytes. The system comprises a sample holder having structures formed thereon for spatially separating and constraining a plurality of light-emitting analytes each having a single nucleic acid molecule or a single nucleic acid polymerizing enzyme, a light source configured to illuminate the sample holder, and an optical assembly configured to collect and detect separately and substantially simultaneously light emissions associated with the plurality of light emitting analytes. The system may further include a computer system configured to analyze the light emissions to determine the structures or properties of a target nucleic acid molecule associated with each analyte.

SUMMARY OF THE INVENTION

Based on this background, it would be advantageous to provide more effective and/or more accurate means for optical processing, particularly in biosensing applications.

This object is addressed by an optical device according to claim 1, a detection apparatus according to claim 2, a method according to claim 3, and a use according to claim 15. Preferred embodiments are disclosed in the dependent claims.

According to a first aspect, an embodiment of the invention relates to an optical device for the processing of light that is associated to a characteristic wavelength and that is called "input light" in the following. The optical device may for example be used in biosensing applications and comprises the following components:

a waveguiding substrate (hereafter briefly referred to as "the substrate") with a first surface and a second surface.

a reflective structure that is disposed on the first surface of the substrate.

a perforated structure that is disposed on the second surface of the aforementioned substrate and that comprises apertures having in at least one direction a diameter that is smaller than the characteristic wavelength of the input light, The reflective structure comprises a diffractive surface within one and the same combined structure that allows diffracting light entering the substrate from outside and reflecting light propagating in the substrate.

The above mentioned "characteristic wavelength" refers to a particular, given value of a wavelength that is suited for characterizing the spectrum of the input light. It may for example be defined as the smallest wavelength of the spectrum, as the wavelength of the maximal intensity (peak) of the spectrum, or as the mean wavelength of the spectrum. Typical values of the characteristic wavelength are about 350 nm, about 450 nm, about 550 nm, about 650 nm, about 750 nm, and about 850 nm. In case fluorescence is excited by the input light, the "characteristic wavelength" typically corresponds to the operating wavelength used for excitation of the fluorophores (having a value of e.g. about 450 nm).

The "waveguiding substrate" may have any design that allows for the propagation of input light. A propagation according to the principles of a waveguide, i.e. with a repeated reflection and/or refraction back to a core, may be enabled by the substrate itself or, preferably, in combination with the perforated structure and the reflective structure (acting as reflective coatings). The substrate may preferably have a planar or flat geometry like that of a plate or layer. Moreover, the first and second surfaces are usually opposite to each other, lying for example on opposite large surfaces of a plate. The second surface of the substrate, which carries the perforated structure, is preferably a (highly) reflecting surface, for example a surface constituted or coated by a metal.

The "perforated structure" may optionally have a flat or planar geometry, too. It may for example be realized as a layer following the contour of the second surface of the substrate. The perforated structure or at least the inner surfaces of its apertures may optionally be constituted by a metal, thus enabling the excitation of an evanescent field inside the apertures (if the apertures are illuminated with light whose polarization is perpendicular to the short side—i.e. the side being shorter than the characteristic wavelength—of the aperture). A perforated structure made of a reflective material may additionally serve to realize the above mentioned reflectivity of the second surface of the substrate. Moreover, the at least one direction in which the diameter of the apertures is smaller than the characteristic wavelength is usually an in-plane direction in a planar perforated structure. The apertures may be filled with some specific, typically transparent material, or they may be "empty" (i.e. filled with the surrounding medium at hand).

As will be explained in more detail with respect to preferred embodiments, the "reflective structure" may just be a uniform layer of a (reflective) material, or it may have some elaborate and optically interactive pattern ("structure" in the narrower sense of the word). The reflective structure may have a flat or planar geometry that typically follows the contour of the first surface of the substrate.

The perforated structure and/or the reflective structure may be disposed directly on the substrate, or there may optionally be one or more intermediate layers in between.

According to a second aspect, an embodiment of the invention relates to a detection apparatus comprising the following components:

- an optical device of the kind described above, i.e. with a waveguiding substrate having a reflective structure and a (preferably metalized) perforated structure on its first and second surface, respectively, wherein apertures in the perforated structure have in at least one direction a diameter that is smaller than a characteristic wavelength of input light. The optical device may be realized by any of its various preferred embodiments described in the present application.
- a light source for emitting input light being associated to said characteristic wavelength into the optical device.
- a light detector for detecting light coming from the optical device.

The light source may be any kind of light source that is suited for the generation of input light having a spectrum with the desired characteristic wavelength. The light source may for example be a monochromatic light source such as a laser unit. The polarization of the light source should be such that the electric field is oriented in plane and perpendicular to the shortest side of the holes (i.e. smaller than the wavelength) in the perforated structure.

The light source will usually be arranged such that the emitted light rays reach a selected surface of the substrate with the angle of incidence lying within some given range.

The light detector may be any device that is suited to detect the light of interest coming from the optical device. It may for example be an imaging device such as a CCD or CMOS chip allowing for the generation of images of the optical device.

The light coming from the optical device that is detected by the light detector may be "primary" input light (after passage through and/or interaction with the optical device), or it may have another origin. In the latter case, the light will typically be "secondary light" that is somehow generated by the input light, for example light of fluorescence that has been stimulated by the input light.

According to a third aspect, an embodiment of the invention relates to a method for the processing of input light that is associated to a characteristic wavelength, said method comprising the propagation of input light in a waveguiding substrate via a reflective structure that is disposed on a first surface of the substrate, such that the propagated input light reaches apertures of a perforated structure on a second surface of said substrate, wherein the reflective structure comprises a diffractive surface within one and the same combined structure that allows diffracting the input light entering the substrate from outside and reflecting the input light propagating in the substrate. The method may particularly be carried out with an optical device or a detection apparatus of the kind described above.

The optical device and the method are based on the same principle, i.e. that input light propagates in a waveguiding substrate, where it can interact with apertures of a perforated structure. Explanations and definitions provided for the optical device (or the detection apparatus) are therefore analogously valid for the method, too, and vice versa.

In the following, various preferred embodiments will be described in more detail that can be realized in combination with the optical device, the detection apparatus and/or the method defined above.

In one basic embodiment, the reflective structure of the optical device comprises a diffractive structure that allows for the diffraction of input light into the substrate. Preferably said reflective structure and diffractive structure are identical, i.e. realized by the same entity. This combined structure will both diffract light, particularly input light entering the substrate from outside, and reflect light, particularly (input) light that propagates in the substrate. The diffractive structure usually constitutes an outer surface of the optical device that is irradiated by the input light during usage.

A method that is associated to the aforementioned embodiment serves for the processing of input light that is associated to a characteristic wavelength and comprises the diffraction of input light into a waveguiding substrate such that the diffracted input light reaches apertures of a perforated structure on a surface of said substrate.

Via the diffraction at the diffractive structure on the first surface of the device, input light can be coupled into the substrate. In order to enhance the interaction of this input light with the perforated structure of the second surface, it is preferred that constructive interference of the input light which has been diffracted occurs at at least one of the apertures of the perforated structure. Thus the intensity of the input light can be concentrated at the aperture(s), yielding a high efficiency of desired effects of the light there.

It should be noted in this context that a suitable design of the reflective/diffractive structure, the substrate, and the perforated structure may be found from theoretical considerations and/or computer simulations. Moreover, a working embodiment may readily be obtained by irradiating some (arbitrary) diffractive structure disposed on a waveguiding medium with input light (under the same conditions, e.g. angle of incidence, that shall later be used during applications) and observing where zones of constructive interference are. The thickness of the waveguiding substrate may then be chosen such that the zones of constructive interference lie on a surface opposite to the reflective structure, and a perforated structure can be manufactured on said surface with its apertures being located just at said zones.

The diffractive structure may for example be realized by a phase grating, i.e. a structure in which the phase of incident light is affected in a spatial pattern. A phase grating may for example be realized by machining an appropriate geometry (e.g. parallel grooves) into the surface of a transparent medium, wherein the remainder of said medium may later serve as waveguide substrate. Of course other realizations of the diffractive structure are possible, too, for example using holographic gratings.

In another basic embodiment of the optical device (or the detection apparatus), the reflective structure comprises a metal layer. Preferably the reflective structure and said metal layer are identical, i.e. realized by the same entity. The metal layer may preferably have a uniform, homogenous ("unstructured") geometry. Typically, its only function is to reflect light back into the substrate.

As the aforementioned metal layer will usually be non-transparent, input light cannot enter the substrate through this layer but will typically have to be coupled in through another surface, e.g. a side face of the substrate. In order to assist this process and to provide for a favorable intensity distribution in the substrate, a grating may be disposed on a side face of the substrate for coupling input light into the substrate. It should be noted in this context that the term "grating" shall substantially have the same meaning as "diffractive structure". In order to avoid confusion, the term "grating" will however primarily be used for a diffractive structure on the side face that is applied in combination with the metal layer on the first surface of the substrate.

In another embodiment, at least one element that is called "bridge" in the following and that is made of an optically conducting material is disposed between the substrate and an aperture of the perforated structure. The diameter of this bridge shall be larger than that diameter of the aperture which is smaller than the characteristic wavelength. Furthermore, the minimum diameter of the bridge is preferably determined by the periodicity of the standing mode wave pattern in the central waveguide, being $p=\pi/\beta_m$. The maximum diameter of the bridge is governed by the guaranteed length over which only a single mode (TE 1st order) propagates inside the waveguide: making the bridge too wide causes the appearance of higher order modes and thus decreases the field incident on the ZMWs. Making the bridge diameter wider also introduces additional scattering. A typical value for the maximum width would be 10% of the bridge/ZMW spacing. Preferably, such a bridge is disposed at every aperture of the perforated structure. Due to its larger diameter, the bridge allows for the transfer of light from the substrate to the aperture even if the intensity peak of said light is not exactly aligned with the aperture, for example due to manufacturing tolerances. The bridge may optionally consist of the same material as the substrate.

The waveguiding substrate may comprise any material that is suited to support the propagation of input light in the desired manner. The material will usually have a high transparency for the input light. In a preferred embodiment, the substrate comprises a dielectric layer, for example a layer of transparent plastic such as poly(methylmethacrylate) (PMMA) or a layer of glass.

The design of at least one of the apertures of the perforated structure is preferably such that it operates as a zero-mode waveguide for the input light. This means that (i) input light that is polarized parallel to the diameter that is smaller than the characteristic wavelength of the input light propagates in the waveguide, while (ii) input light with polarization perpendicular to this diameter does not propagate (in this case a non-propagating evanescent field will be introduced).

The apertures of the perforated structure may in general have any irregular or regular geometrical shapes, sizes and/or distribution (as long as they have in at least one direction a diameter that is smaller than the characteristic wavelength of the input light). Preferably, all apertures may have the same shape and/or size and/or be distributed in a regular manner across the perforated structure. At least one of the apertures may optionally have an elongated shape (e.g. of a straight line), wherein the diameter of the aperture that is smaller than the characteristic wavelength will in this case typically be measured perpendicular to the axis of elongation. Additionally or alternatively, at least one of the apertures may have a compact shape such as the shape of an ellipse or circle.

Preferably all apertures of the perforated layer have the same shape and size and are oriented parallel to each other.

In a preferred embodiment the perforated structure comprises a wiregrid, i.e. a structure with parallel line-like apertures separated by intermediate material ("wires"). Said intermediate material may for instance be a metal that reflects the input light.

The input light may preferably be polarized light. Most preferably, the polarization is such that the input light is maximally reflected back into the substrate by the perforated structure. This condition is for example fulfilled if the direction of polarization is perpendicular to the direction in which the diameter of the apertures is smaller than the characteristic wavelength.

The perforated structure may optionally comprise application-specific substances, for example detection probes. Such substances will usually be located on the outside of the perforated structure (i.e. on its surface opposite to the substrate and/or in the apertures) such that they can be accessed by a medium to be processed and/or examined. The application-specific substances may for example be nucleotide sequences that serve as replication templates.

In one preferred embodiment, evanescent waves generated at the apertures of the perforated structure may excite fluorescence in adjacent sample material. This approach can particularly be used to monitor surface specific processes such as the incorporation of mononucleotides into a strand of replicated nucleic acids (such as DNA, cDNA), wherein the excited fluorescence allows for determining which nucleotide (A, T, G, C) is presently incorporated if these mononucleotides are labeled with different fluorophores. Details about such an approach may for example be found in the US 2011/10210094 A1.

The invention further relates to the use of an optical device or a detection apparatus of the kind described above for sequencing nucleic acids, molecular diagnostics, biological sample analysis, chemical sample analysis, food analysis, and/or forensic analysis.

BRIEF DESCRIPTION OF THE DRAWINGS

These and other aspects of the invention will be apparent from and elucidated with reference to the embodiments described hereinafter. In the drawings.

Like reference numbers or numbers differing by integer multiples of 100 refer in the figures to identical or similar components.

DETAILED DESCRIPTION OF EMBODIMENTS

The invention will in the following be explained with respect to a biosensing application, particularly the sequencing of nucleic acids, though it can of course be used in many other applications, too.

Currently most of the commercially available systems for (DNA or RNA) sequencing use some form of clonal amplification to boost the signal to be detected and thereby to improve signal-to-noise ratio (SNR). This has three disadvantages:

A more complex sample preparation protocol/process is needed, which makes the desirable, ultimate integration of all process steps in a "sample-in result-out" system considerably more difficult as well as more costly.

A PCR amplification step is needed which introduces bias as PCR amplifies some regions of the DNA better than others. This skewed amplification may and will distort the balance in variations found in DNA under examination and therefore is not desirable when considering clinical application of DNA (and RNA) sequencing data.

Amplification eliminates the methylated C (which are biologically important as the methylation of C nucleotides is key in silencing of genes) and turns them into "normal" un-methylated Cs.

There is a single sequencing system on the market which does not use clonal amplification but does single molecule sequencing and real-time detection of the nucleotide incorporation process (RS DNA sequencer of Pacific Biosciences, California). Owing to this latter feature this system can detect the methylated C by the longer time it takes the polymerase to incorporate the methylated C (J. Eid et al., Science 323, 133-138, 2009).

Despite these positive attributes from a standpoint of the biological useful information being provided, the aforementioned system suffers from a major drawback in that a high power and thus large laser is needed. In the commercial system a 30 W laser has to be used. This means that the system is too expensive to enable widespread adoption and use in clinical diagnostics practice.

In view of the above, two approaches will be discussed in the following with respect to FIGS. 1-3 and 4-6, respectively. The approaches use diffractive optical structures in order to achieve a more efficient evanescent field excitation: one in which the excitation is in-plane and an alternative in which the excitation is along the plane of ZMWs. The first embodiment that is proposed here makes the excitation of a zero-mode waveguide structure needed for single molecule detection far more efficient by using a wiregrid coupled to a waveguide in which the light is coupled in by a diffraction grating.

Figure 1:
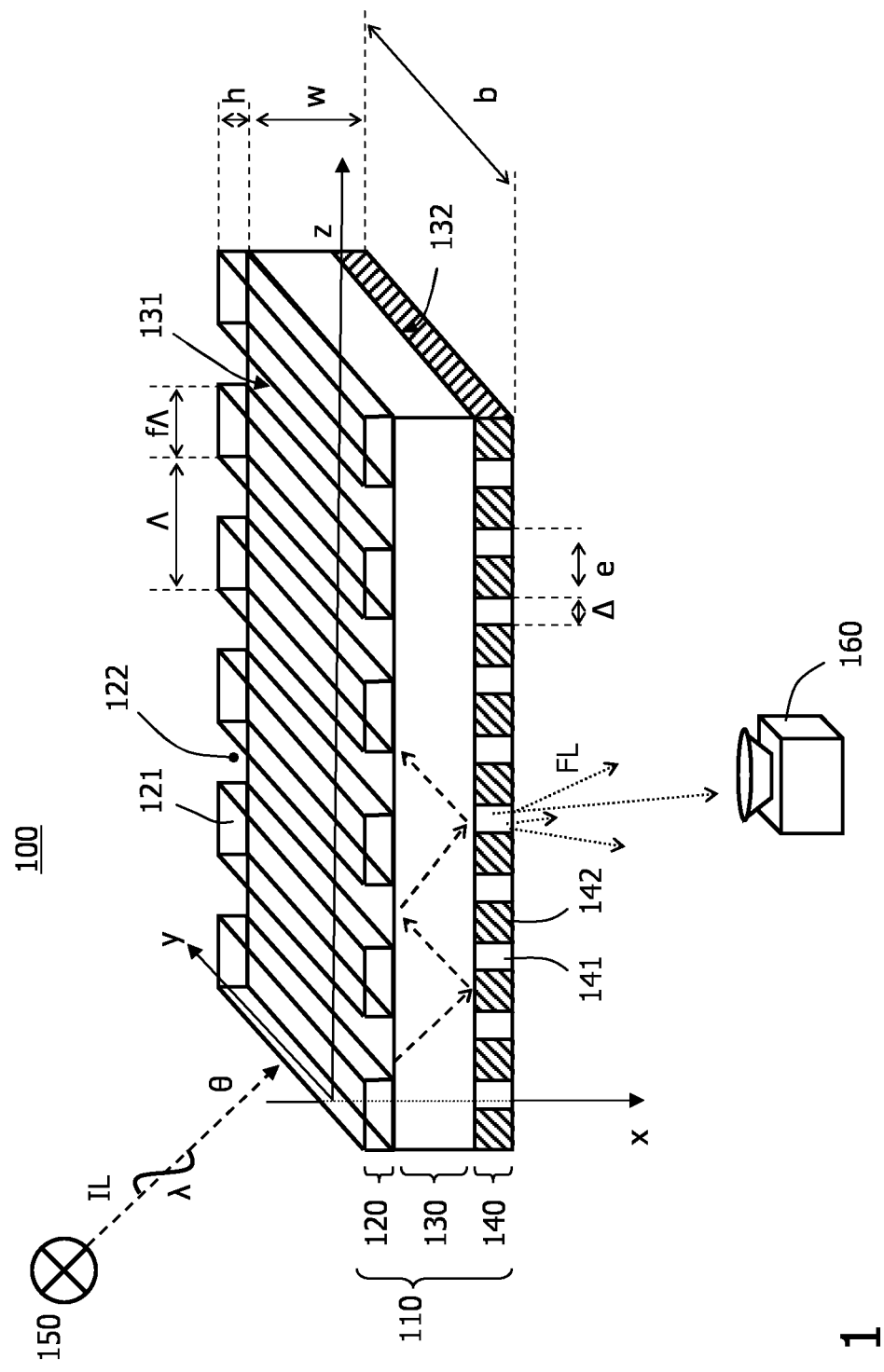
FIG. 1 schematically shows a perspective view of a detection apparatus comprising a first optical device with a diffractive structure according to an embodiment of the present invention.

FIG. 1 schematically shows a detection apparatus 100 according to an embodiment of the aforementioned approach. The detection apparatus 100 comprises three essential elements:

A light source 150 for emitting input light IL having a characteristic wavelength λ. The light source may for example be a laser emitting substantially monochromatic light of a wavelength λ that typically ranges between about 350 nm and 800 nm, wherein said wavelength constitutes the "characteristic wavelength λ" in this example. If emission with a broader spectrum occurs, the "characteristic wavelength λ" may for example be defined as the smallest wavelength of this spectrum. Preferably, the emitted light is linearly polarized in y-direction (i.e. parallel to the grid lines of the perforated structure 140).

An optical device 110 comprising a waveguiding substrate 130 with a reflective structure 120 on a first (top) surface 131 and a perforated structure 140 on a second (bottom) surface 132. Because an essential feature of the reflective structure 120 is (in this embodiment) that it is also diffractive, it will in the following be called "diffractive structure" 120. The optical device 110 is substantially planar, extending with a thickness w parallel to an z,y-plane, wherein the input light IL is incident onto this plane under an angle θ (with respect to the x-axis).

A light detector 160 for detecting light FL coming from the optical device 110, particularly from the perforated structure.

In the shown example, the perforated structure 140 is a "wiregrid" comprising line-shaped apertures 141 or grooves that extend in y-direction parallel to each other (extending in x-direction through the complete perforated structure 140) and that are separated by small wires 142 of metal (e.g. aluminum). The waveguiding substrate 130 together with the perforated structure or wiregrid 140 on its bottom surface constitutes what is in the following called a "wiregrid substrate".

A wiregrid substrate generally consists of a dielectric (glass or plastic) substrate having on one side a thin metallic layer with small holes acting as zero-mode waveguides. Zero-mode waveguides are an efficient means for producing a well-localized very thin electro-magnetic field near the surface of a dielectric interface. In combination with surface-specific biochemistry (e.g. binding of specific analytes to surface bound antigens) the zero-mode waveguides can be used for the detection of certain proteins or DNA-fragments in human samples like blood or saliva. In the above mentioned RS DNA sequencer of Pacific Biosciences a technique called SMRT (single molecule real-time) is being used for real-time detection of DNA sequencing, claiming faster, more efficient and more accurate sequencing results (Lundquist et al., "Parallel confocal detection of single molecules in real time", Opt. Lett. 33(9), 2008, p. 1026). Such a system can use a substrate comprising a 2D array of zero-mode waveguides (ZMW), each ZMW being capable of real-time monitoring the incorporation of the successive nucleotides by a single polymerase molecule. Distinguishing between the different nucleotides A, C, G and T can be done using fluorescence detection, where each of the four nucleotides is labeled with a different fluorescent group. For an efficient DNA sequencing $10^5$ to $10^6$ of these ZMW detection chambers are required on a single cartridge. Reading the fluorescence from all these ZMWs at the same time, with sufficient SNR, requires a high power (several tens of Watts) laser system for exciting the ZMWs. For this reason a corresponding product is limited to real-time fluorescence detection of approximately $10^4$ ZMWs.

These problems are addressed by the proposed novel optical device that comprises a metallic wiregrid substrate (acting as ZMW) at one side and a diffraction structure, e.g. a phase grating, at the other side. This optical device acts as a kind of optical waveguide, (i) redistributing the energy contained in the excitation beam IL underneath the whole wiregrid and (ii) simultaneously creating regions of enhanced intensity at the position of the ZMWs. Using this optical device allows for the creation of an electromagnetic field intensity at the position of the ZMWs that is one to two orders of magnitude stronger, compared to the excitation of these ZMWs using far field focusing of light, i.e. without waveguiding means.

The apertures or holes in the wiregrid substrate may be rectangular or circular shaped as long as the dimension in one direction is well below the wavelength of the excitation light. In this way input light with a polarization in the direction of this sub-wavelength dimension (TM-polarization) is transmitted by the wiregrid, whereas the perpendicular polarization (TE) is 100% reflected and will create an evanescent field inside the aperture. As a result, surface specific optical sensing can be achieved by illuminating the wiregrid substrate with TE-polarized light.

In FIG. 1 the wiregrid 140 ("perforated structure") consists of a regular array of metallic stripes 142 at the bottom side of the substrate 130. In z-direction, the distance e between two neighboring wires 142 is about 1 μm, and the width A of the apertures 141 in between two wires is in the order of 100 nm. In y-direction, the length b of the apertures 141 may for example be in the order of 100 µm, though there is in principle no limitation to it.

On top of the substrate 130 a phase grating 120 is deposited. The purpose of this phase grating is twofold:
(i) The grating diffracts the incoming light IL inside the substrate 130, where the different diffraction orders are henceforth multiple reflected at the metallic interface of the wiregrid 140, and the diffraction grating 120 itself (acting as a "reflective structure"). The substrate 130 bounded by the diffraction grating 120 and the metallic layer 140 thereby acts as a waveguide, redistributing the light inside the substrate.
(ii) By carefully choosing the appropriate geometry of the optical device 110 (e.g. thickness w and refractive index $n_2$ of the substrate 130, grating pitch A and fill factor f), the diffracted orders interfere constructively at the positions of the apertures 141 (ZMWs), thereby exciting the required evanescent field inside the ZMW holes.

Moreover, the light detector (or an additional light detector) could be arranged at other positions, too. With respect to FIG. 1, it could for example be disposed above the optical device 110 (i.e. on the same side as the light source in this embodiment). In this case fluorescence light FL does not have to pass through the sample medium before reaching the detector.

The optical geometry as depicted in FIG. 1 has been simulated using an analytical approach, summing the reflection coefficients for the different diffraction orders inside the substrate whilst being multiple reflected between metal and grating layer. Also a finite element method has been used to solve Maxwell's equations for the above geometry. Both the analytical and FEM results were in good agreement.

The thickness w of the substrate 130 can be tuned such that well-defined intensity maxima coincide with the bottom side 132 of the substrate, at the interface to the metallic layer 140 comprising the ZMWs 141. The aim of the study was to calculate the magnitude of the electric field at the position of a ZMW compared to the magnitude of the incoming electric field of the exciting beam IL.

Figure 2:
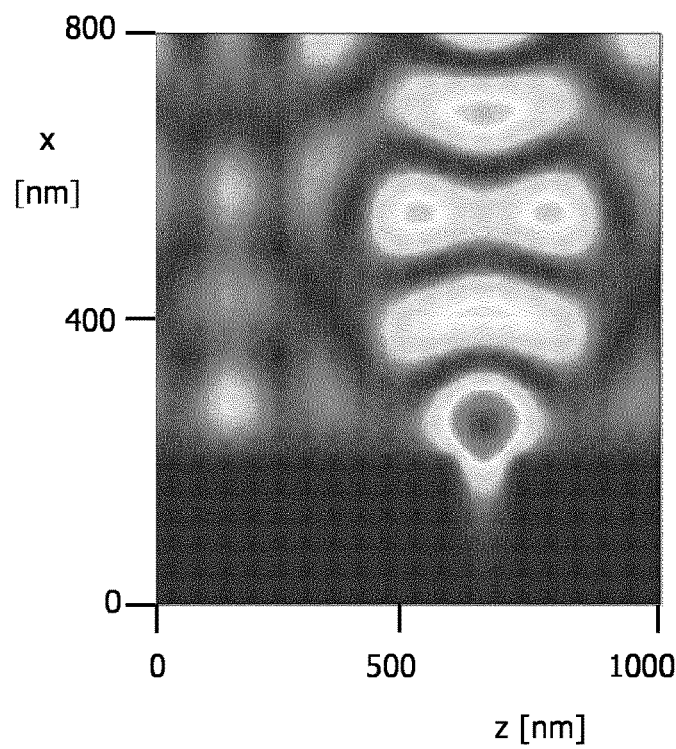
FIG. 2 shows a calculated intensity distribution of the electrical field behind a phase grating.

FIG. 2 shows an example of FEM calculations for a grating with grating period $\Lambda=1$ µm, excitation wavelength $\lambda=450$ nm, refractive index of the substrate $n_2=1.6$, grating height $h=500$ nm and grating fraction $f=0.7$. The diagram corresponds to the waveguiding substrate 130 and the perforated structure 140 of FIG. 1 (upside down) in the associated x,z coordinates. For a substrate thickness of $w=33$ µm, one can clearly see a well-localized spot of high intensity at the edge of the substrate, where the ZMW is located. The lateral dimensions of this intensity spot are very small, creating a relatively high electric field component.

Figure 3:
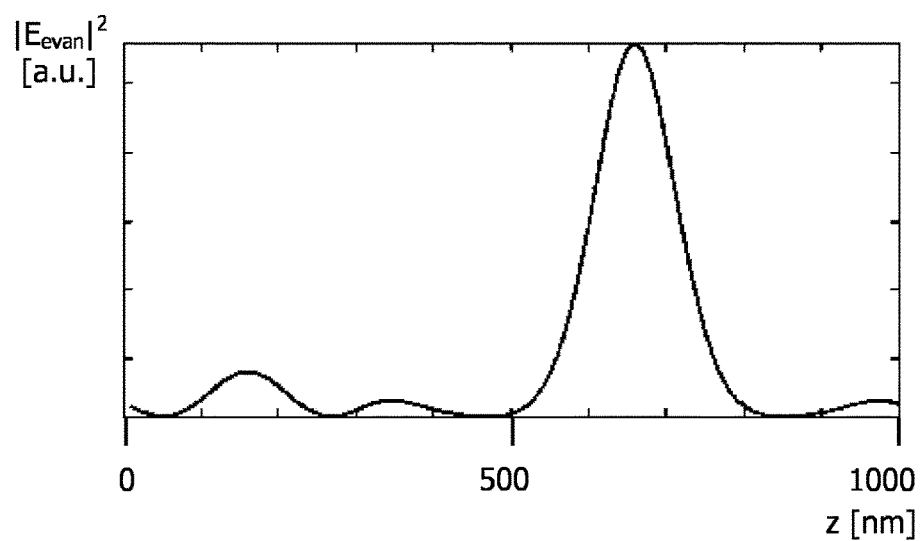
FIG. 3 shows a diagram of the intensity variation resulting from the situation of FIG. 2 along the surface of a waveguiding substrate.

In order to estimate the efficiency of this method compared to e.g. far field focusing of a beam of light onto a ZMW, the electric field distribution at the metal-substrate interface 132 was determined using FEM calculations for an incoming overall excitation intensity of $|E_{input}|^2=1$ and for $\lambda=450$ nm. The result of this calculation is shown in FIG. 3. The increase in electromagnetic energy density U at the metal interface is given by the formula:

$$\frac{U_{evan}}{U_{input}} = \frac{\varepsilon_{substrate} \cdot |E_{evan}|^2}{\varepsilon_{air} \cdot |E_{input}|^2} = \sqrt{n_{substrate}} \cdot |E_{evan}|^2$$

leading to a gain in energy density of a factor of 35.5.

A proper figure of merit when comparing the binary phase grating with plane bulk illumination of $N_{ZMW}$ zero mode waveguides, is the ratio between the energy density $U_{evan}$ of the evanescent electric field inside the ZMWs to the required overall input power of the excitation beam. For a straightforward comparison let us assume that the ZMWs have a footprint $A_{ZMW}$ of $0.1 \times 100$ µm² and that they are separated $p=1$ µm apart. The efficiency $\eta$ for the binary phase grating (BPG) can now be expressed as:

$$\eta_{BPG} = \frac{U_{evan}}{P_{input}} = \left(\frac{U_{evan}}{U_{input}}\right)_{BPG} \cdot \frac{1}{c \cdot A_{input}} =$$

$$35.5 \cdot \frac{1}{c \cdot N_{ZMW} \cdot 1 \cdot 100 \ \mu m^2} = \frac{1.18 \cdot 10^3}{N_{ZMW}} \left[\frac{J/m^3}{W}\right]$$

In order to make a fair comparison between BPG and plain far field illumination of a series of ZMWs, the evanescent field inside the ZMWs is estimated for far field excitation by calculating the overlap of a diffraction limited Airy illumination profile and the ZMW geometry. For a rectangular shaped ZMW with dimensions $0.1 \times 100$ µm² and a typical focusing NA of 0.8 this overlap is $\eta_{Airy}=P_{ZMW}/P_{Airy}=0.17$. The energy density inside a single ZMW is then given by $$U_{evan} = I_{evan}/c = \frac{P_{ZMW}}{A_{ZMW} \cdot c} = \frac{\eta_{Airy}}{A_{ZMW} \cdot c} \cdot \frac{P_{input}}{N_{ZMW}}$$

resulting in an efficiency for far field (FF) illumination of:

$$\eta_{FF} = \frac{U_{evan}}{P_{input}} = \cdot \frac{\eta_{Airy}}{c \cdot A_{ZMW} \cdot N_{ZMW}} = \frac{56.7}{N_{ZMW}} \left[\frac{J/m^3}{W}\right]$$

By using a grating, an increase in excitation efficiency of a factor of 21 can hence be achieved for this specific example, consisting of a 1D-array of linear ZMWs (wiregrid substrate).

The above analysis has been performed for a linear wiregrid 140, using linear ZMWs 141. For a 2D-array of circular ZMWs, it has been shown that
(i) using the proposed grating-metal waveguide the light can also be upconcentrated in two dimensions, leading to an even further evanescent field intensity gain of $U_{evan}/P_{input}$, and
(ii) the gain in illumination efficiency compared with 2D-focussing is another factor of about 10 because of the 2-dimensional Airy spot distribution of about $1 \times 1$ µm² that has to be mapped onto the ZMW with size $0.1 \times 0.1$ µm².

For a 2D-array of metallic ZMWs the overall coupling of optical power inside the ZMW may be a factor 100 to 1000 more efficient as compared to far field focusing using a micro-lens array.

Figure 4:
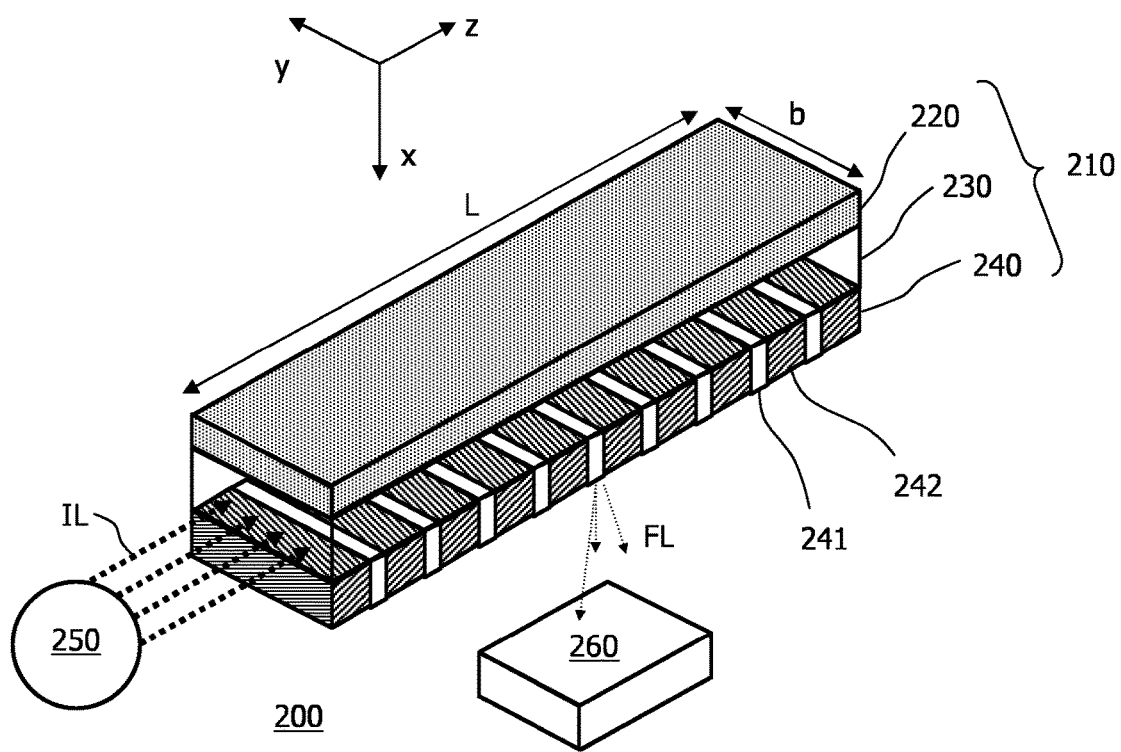
FIG. 4 schematically shows a perspective view of a detection apparatus comprising a second optical device with a metal layer as reflective structure.

FIG. 4 shows schematically a perspective view of a detection apparatus 200 with a light source 250, a light detector 260, and an optical device 210 according to an alternative proposal.

As above, the optical device 210 comprises a wiregrid substrate consisting of a waveguiding substrate 230 together with a perforated structure or wiregrid 240 on its bottom surface. The top surface of the substrate 230 is now covered by a reflective structure in the form of a metal layer 220. As the top and bottom layers on the substrate both preferably consist of metal, the optical device 200 will in the following also be called Metal-Insulator-Metal ("MIM") waveguide. It should be noted that the definition of the coordinate system is different from that of FIG. 1.

The light source 250 and the light detector 260 may substantially be the same as in the apparatus 100 discussed above, but the arrangement of the light source 250 is now such that it illuminates (perpendicularly) a side face of the substrate 230.

The MIM-waveguide 210 provides an alternative design to increase the local intensity at the ZMW positions 241 of the wiregrid 240 by guiding the input light IL in a thin layer just above the ZMW wiregrid plane. Since the core of the waveguide substrate 230 has a much smaller cross sectional area (x,y-plane) than the area illuminated in the above grating design of the optical device 110, one would expect to achieve a larger gain in overall excitation efficiency using this MIM waveguide solution. The TE-polarized field inside the MIM will propagate as a sum of several TE polarized guided modes of which the propagation constants $\beta_m$, as given by the equations below, are real valued. The part of the total field distribution that propagates in the positive z-direction is given by (with $k_0=2\pi/\lambda$, n being the refractive index and d the height of the waveguide, cf. FIG. 5):

$$E_{total}(x, z) = \sum_m \sum_{y,m}(x, z)$$

$$E_{y,m}(x, z) = a_m u_m(x) \exp(-j\beta_m z)$$

$$u_m(x) = \begin{cases} \sqrt{\frac{2}{d}} \cos\left(\frac{m\pi x}{d}\right), & m = 1, 3, 5 \ldots \\ \sqrt{\frac{2}{d}} \sin\left(\frac{m\pi x}{d}\right), & m = 2, 4, 6 \ldots \end{cases}$$

$$a_m = \sqrt{2d} \, E_0$$

$$\beta_m = \sqrt{(k_0 n)^2 - \frac{m^2 \pi^2}{d^2}}$$

For maximum coupling of the field into the ZMWs, the field maxima of the propagating modes need to coincide with the actual positions of the zero mode waveguides 241. Furthermore, ideally only a single mode (m) should propagate inside the waveguide in order to ensure a rather uniform intensity distribution along the propagation direction of the mode.

Figure 5:
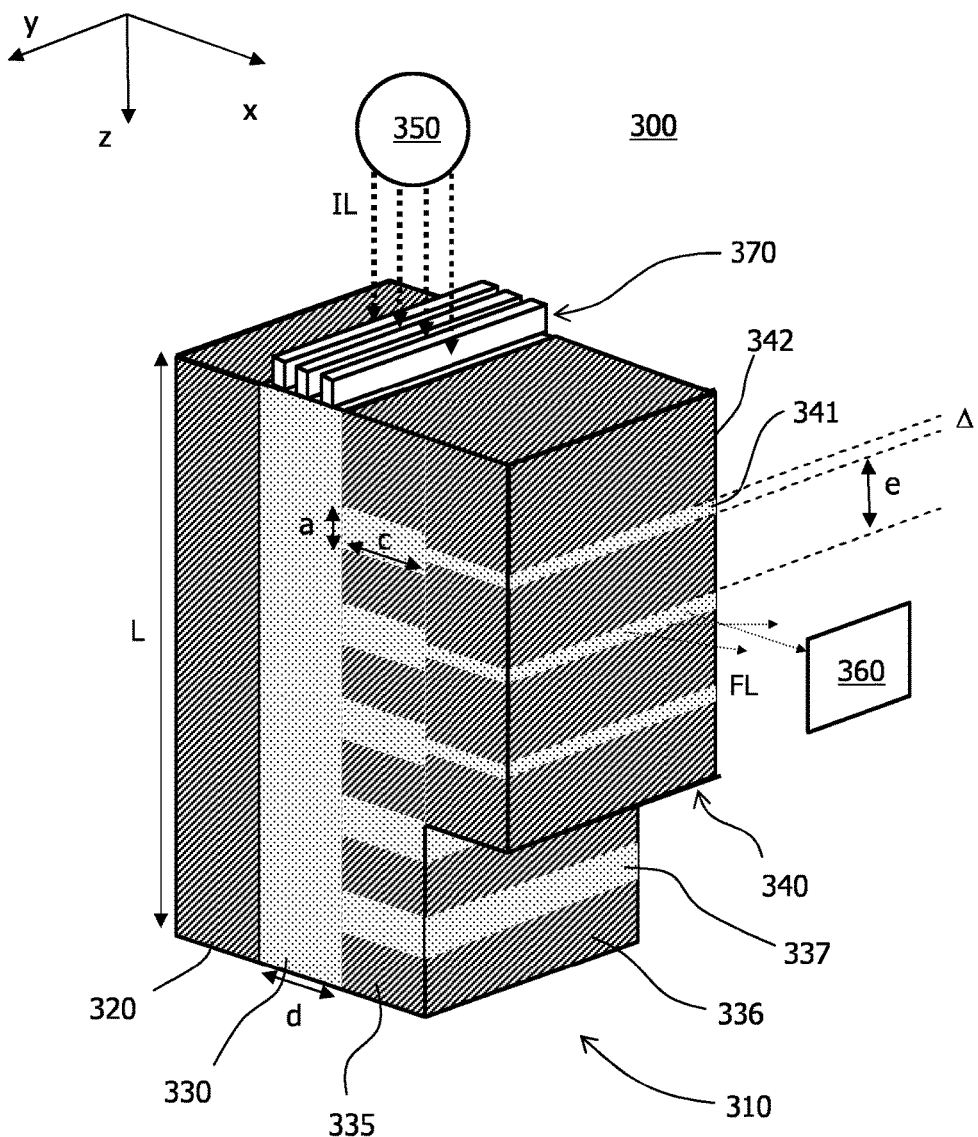
FIG. 5 schematically shows a perspective view of a detection apparatus comprising a third optical device with a metal layer as reflective structure and a bridge structure.

The latter may be achieved by using a binary grating on top of the substrate and matching the propagation constant of one of the grating orders to the propagation constant $\beta_m$ of a specific waveguide mode m. FIG. 5 shows an embodiment of such a detection apparatus 300 with a light source 350, a light detector 360, and a modified optical device 310. The optical device 310 has a grating 370 (or, more generally, a diffractive structure) on the side face through which the input light IL is coupled into the waveguiding substrate 330.

The optical device 310 of FIG. 5 additionally addresses another aspect, too:

Due to the finite length L of the waveguide, the propagating mode m will be reflected back and forth leading to a standing wave pattern inside the waveguide with periodicity $p=\pi/\beta_m$. The exact locations of the corresponding intensity maxima thereby strongly depend on the waveguide dimensions L and d. As a result the local intensity at the position of the ZMWs 341 may rely on manufacturing tolerances of the waveguide. This issue can be addressed by incorporating an intermediate "bridge" waveguide 337 between each ZMW 341 and the substrate 330 (it should be noted that only a part of the vertical extension of the wiregrid 340 is shown). The bridges 337 preferably have a width, a, of several standing wave periodicities p and effectively transfer the core mode intensity towards the ZMWs. A typical value for the maximum of the width "a" is about 50%, about 40%, about 30%, about 20%, about 16%, about 12%, about 10%, or about 5% of the spacing e between neighboring ZMWs. In general, e is typically such that the ratio a/e does not exceed a value between 0.05 and 0.50 (in steps of 0.01). The spacing e between neighboring ZMWs typically ranges between about 0.5 μm and about 10 μm, though other values are possible, too.

Figure 6:
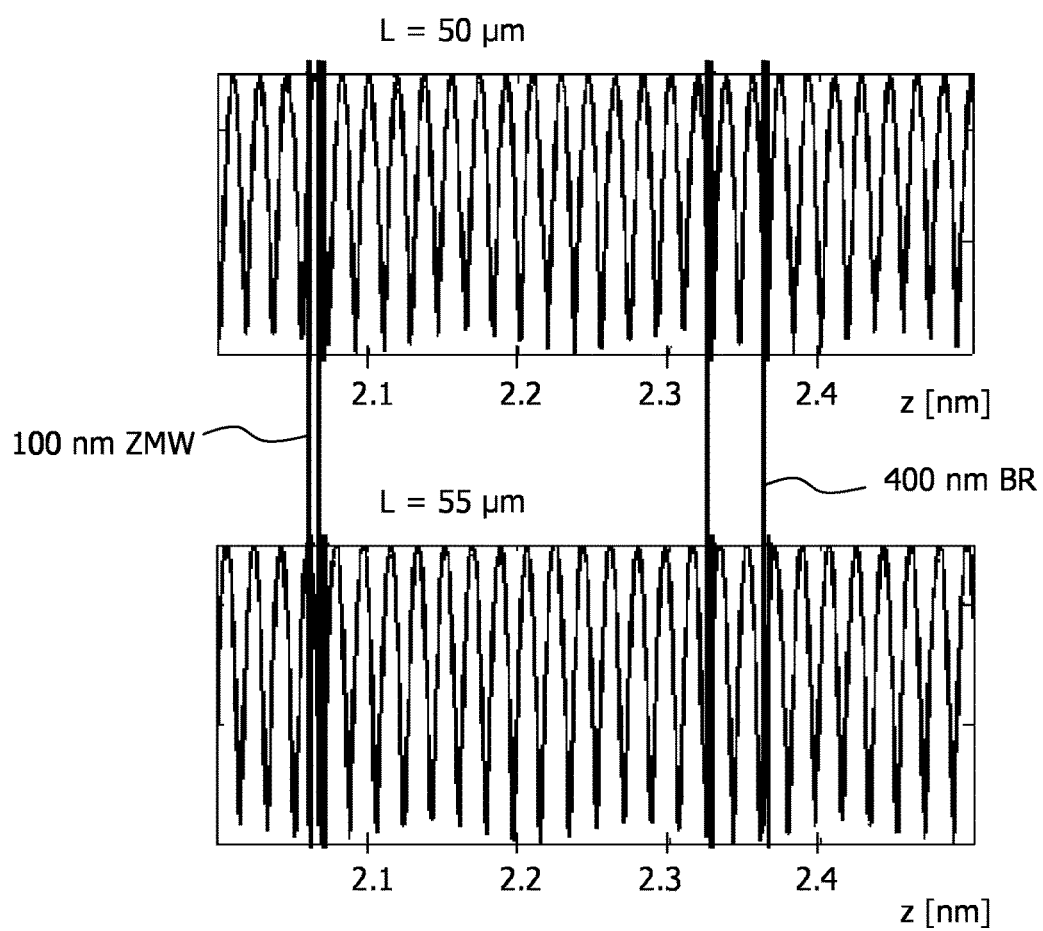
FIG. 6 is a diagram showing the calculated mean of the magnitude of the electric field at a section of the waveguide of FIG. 5.

The latter is illustrated in the diagrams of FIG. 6 in which the mean of the magnitude of the electric field (vertical axis, arbitrary units, m=3) at a section of the waveguide is plotted with the distance along the axis x for two values of L, namely L=50 μm (top diagram) and L=55 μm (bottom diagram). With a ZMW of 100 nm width (position shown by left pair of vertical lines), the coupled field will vary with L. However with a bridge BR of width around 400 nm (position shown by right pair of vertical lines) the total coupled field becomes largely invariant to changing L. Effective and uniform coupling of the central mode intensity by these bridge structures to the ZMWs has been verified using analytical calculations and FEM simulations.

In summary, the described embodiments use a zero-mode waveguide as an efficient way of surface sensitive detection of molecules or particles. When illuminated under the right conditions, in a zero-mode waveguide no light (i.e. no mode) is allowed to propagate. Only an exponential decaying evanescent field is present in between the neighboring (e.g. metallic) walls of a wiregrid. In one embodiment, the proposed novel biosensor structure comprises (i) a wiregrid substrate acting as zero-mode waveguide, and (ii) a diffraction grating for efficient coupling of the illumination intensity in the zero-mode waveguides. Electro-magnetic field calculations show that two orders of magnitude can be gained with respect to excitation intensity using such a structure, resulting in an increase of detection SNR which may be used for a reduction of the measurement time with a factor of hundred or alternatively could be used to reduce the required laser power.

The invention can inter alia be used in the field of biosensing, in particular for nucleic acid sequencing applications where many detector sites need to be monitored simultaneously real-time.

It follows a list of embodiments of the present invention:
embodiment 1: An optical device for the processing of input light that is associated to a characteristic wavelength λ, comprising:
   a waveguiding substrate 130, 230, 330 with a first surface 131 and a second surface 132;
   a reflective structure 120, 220, 320 that is disposed on the first surface of the substrate 130, 230, 330;
   a perforated structure 140, 240, 340 that is disposed on the second surface of said substrate 130, 230, 330 and that comprises apertures 141, 241, 341 having in at least one direction a diameter Δ that is smaller than the characteristic wavelength λ.
embodiment 2: A detection apparatus comprising:
   an optical device 110, 210, 310 according to embodiment 1;
   a light source 150, 250, 350 for emitting input light IL that is associated to a characteristic wavelength λ into the optical device 110, 210, 310;

a light detector 160, 260, 360 for detecting light FL coming from the optical device 110, 210, 310.

embodiment 3: A method for the processing of input light IL that is associated to a characteristic wavelength λ, said method comprising the propagation of the input light IL in a waveguiding substrate 130, 230, 330 such that it reaches apertures 141, 241, 341 of a perforated structure 140, 240, 340 on a surface 132 of said substrate 130, 230, 330.

embodiment 4: The optical device 110 according to embodiment 1, wherein the reflective structure comprises a diffractive structure 120 that allows for the diffraction of input light IL into the substrate 130.

embodiment 5: The optical device 110 according to embodiment 4, wherein it is designed such that constructive interference of the input light IL occurs at the apertures 141 of the perforated structure 140.

embodiment 6: The optical device 110 according to embodiment 4, wherein the diffractive structure comprises a phase grating 120.

embodiment 7: The optical device 210, 310 according to embodiment 1, wherein the reflective structure comprises a metal layer 220, 320.

embodiment 8: The optical device 310 according to embodiment 7, wherein a grating 370 is disposed on a side face of the substrate 330 for coupling input light IL into the substrate 330.

embodiment 9: The optical device 310 according to embodiment 1, wherein at least one bridge 337 of an optically conducting material is disposed between the substrate 330 and an aperture 341 of the perforated structure 340, wherein the diameter a of the bridge 337 is larger than the diameter Δ of the aperture which is smaller than the characteristic wavelength λ.

embodiment 10: The optical device 110, 210, 310 according to embodiment 1 or the method according to embodiment 3, wherein the waveguiding substrate 130, 230, 330 comprises a dielectric layer.

embodiment 11: The optical device 110, 210, 310 according to embodiment 1 or the method according to embodiment 3, wherein at least one of the apertures 141, 241, 341 of the perforated structure 140, 240, 340 is a zero-mode waveguide.

embodiment 12: The optical device 110, 210, 310 according to embodiment 1 or the method according to embodiment 3, wherein the perforated structure comprises a wire grid 140, 240, 340.

embodiment 13: The optical device 110, 210, 310 according to embodiment 1, the detection apparatus 100 according to embodiment 2, or the method according to embodiment 3, wherein the input light IL is polarized, preferably such that the polarization direction is perpendicular to the direction of the diameter Δ that is smaller than the characteristic wavelength λ.

embodiment 14: The optical device 110, 210, 310 according to embodiment 1 or the method according to embodiment 3, wherein the perforated structure 140, 240, 340 comprises application-specific substances, particularly detection probes such as nucleotide sequences.

embodiment 15: Use of the optical device 110, 210, 310 of embodiment 1 or the detection apparatus 100 of embodiment 2 for sequencing nucleic acids, molecular diagnostics, biological sample analysis, chemical sample analysis, food analysis, and/or forensic analysis.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An optical device for processing input light that is associated with a characteristic wavelength, comprising:
a waveguide substrate with a first surface and a second surface;
a reflective structure disposed on the first surface; and
a perforated structure disposed on the second surface that comprises apertures having in at least one direction a diameter that is smaller than the characteristic wavelength; wherein the reflective structure comprises a diffractive structure that allows diffracting light to enter the substrate from outside into the substrate and reflecting light to propagate in the substrate.

2. A detection apparatus, comprising:
an optical device for processing input light that is associated with a characteristic wavelength, including:
a waveguide substrate with a first surface and a second surface;
a reflective structure disposed on the first surface; and
a perforated structure disposed on the second surface that comprises apertures having in at least one direction a diameter that is smaller than the characteristic wavelength, wherein the reflective structure comprises a diffractive structure that allows diffracting light to enter the substrate from outside into the substrate and reflecting light to propagate in the substrate;
a light source for emitting the input light into the optical device; and
a light detector for detecting light coming from the optical device.

3. A method for processing input light associated with a characteristic wavelength, the method comprising:
propagating the input light in a waveguide substrate via a reflective structure disposed on a first surface of the substrate, such that the input light reaches apertures of a perforated structure on a second surface of said substrate, wherein the second surface comprises apertures having in at least one direction a diameter that is smaller than the characteristic wavelength, and wherein the reflective structure comprises a diffractive structure;

diffracting the input light entering the substrate from outside into the substrate; and reflecting the input light propagating in the substrate.

4. The optical device according to claim 1, wherein constructive interference of the input light occurs at the apertures of the perforated structure.

5. The optical device according to claim 1, wherein the diffractive structure comprises a phase grating.

6. The optical device according to claim 1, wherein the waveguide substrate comprises a dielectric layer.

7. The optical device according to claim 1, wherein at least one of the apertures of the perforated structure is a zero-mode waveguide.

8. The optical device according to claim 1, wherein the perforated structure comprises a wire grid.

9. The optical device according to claim 1, wherein the input light is polarized, such that the polarization direction is perpendicular to the direction of the diameter that is smaller than the characteristic wavelength.

10. The optical device according to claim 1, wherein the perforated structure comprises application-specific substances that include probes.

\* \* \* \* \*